US005863731A

United States Patent [19]

Romaine et al.

[11] Patent Number: 5,863,731

[45] Date of Patent: Jan. 26, 1999

[54] **POLYMERASE CHAIN REACTION-BASED DIAGNOSTIC TEST FOR THE DETECTION OF *XANTHOMONAS CAMPESTRIS* PATHOVAR PELARGONII**

[75] Inventors: C. Peter Romaine, State College; Gary W. Moorman, Port Matilda; Michael A. Sulzinski, Scranton, all of Pa.

[73] Assignee: The Penn State Research Foundation, University Park, Pa.

[21] Appl. No.: 742,297

[22] Filed: Nov. 1, 1996

[51] Int. Cl.[6] .............................. C12Q 1/68; C12P 19/34; C07H 21/04

[52] U.S. Cl. .......................... 435/6; 435/91.2; 435/252.3; 435/320.1; 536/24.32; 536/24.33; 536/25.3

[58] Field of Search ........................... 435/6, 91.2, 252.3, 435/320.1; 536/24.32, 24.33, 25.3

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis et al. | 435/91 |
| 5,411,941 | 5/1995 | Grinna et al. | 514/12 |
| 5,420,009 | 5/1995 | Hartung et al. | 435/6 |
| 5,427,932 | 6/1995 | Weier et al. | 435/91.2 |

OTHER PUBLICATIONS

Knauss and Tammen, (1967) *Phytopathology* 57:1178–1181.

Lazo et al., (1987) *Int. J. Syst. Bacteriol.* 37: 214–221.

Benedict et al., (1990) *Appl. Environ. Microbial* 56: 572–574.

Anderson & Nameth, (1990) *Phytopathology* 80: 357–360.

Vauterin et al., (1990) *Syst. Appl. Microbiol.* 13: 166–176.

Vauterin et al., (1991) *Gen. Microbiol.* 137: 1677–1687.

Rasmussen & Reeves, (1992) *J. Biotechnol.* 25: 203–220.

Seal et al. (1992) *Appl. Environ. Microbiol.* 58: 3751–3758.

Manulis et al., (1992) *Phytoparasitica* 20: 263.

Hartung et al., (1993) *Appl. Environ. Microbiol.* 59: 1143–1148.

Judd et al. (1993) *Appl. Environ. Microbiol.* 59: 1702–1708.

Manulis et al. (1994) *Appl. Environ. Microbiol.* 60: 4094–4099.

Sulzinski et al., (1995) *J. Phytopathology* 143: 429–433.

Versalovic et al., (1991) *Nucleic Acids. Res.* 19: 6823–6831.

Tuinier et al., (1989), *Plant Diseases*, 73: 875–878.

Hartung et al., (1993), *Plant Diseases*, 76: 889–893.

Sulzinski et al., J. Phytopathol. 144, 393–398 (1996).

Sulzinski et al., J. Phytopathol. 145, 213–215 (1997).

*Primary Examiner*—Kenneth R. Horlick
*Attorney, Agent, or Firm*—Thomas J. Monahan

[57] ABSTRACT

This invention provides methods and reagents for screening plants, particularly geraniums, for infections with bacterial pathogens. Specifically, the invention provides nucleic acid amplification and detection methods for specifically detecting a certain pathovar of a bacterial infectious agent in geraniums. The invention provides a nucleic acid hybridization probe that is specific for *Xanthomonas campestris* pathovar pelargonii, and paired sets of oligonucleotide primers for polymerase chain reaction-catalyzed amplification of DNA fragments comprising the nucleic acid sequences of the invention specific for *Xanthomonas campestris* pathovar pelargonii template DNA. The invention also provides PCR-based methods for detecting *Xanthomonas campestris* pathovar pelargonii DNA, and in particular for distinguishing pathovar DNA from the DNA of the host infected plant. Methods for producing detectably-labeled hybridization probes using PCR are also provided.

34 Claims, 11 Drawing Sheets

```
ATGTAAGCTC CTGGGGATTC ACGAGCTGAA TCGTGATTTG CCGGCAGTGT GGCAAGGCAC  60
GCGCTACCAA AAGGCAAAGA GTGACGTCTT CCCCTACAGA AGCGCTGTCG GCGCGGATTC 120
CAATAGCCTG GTGAAAGCCG GCAAATACGA CATGTCGATG GCCTATATGG AATATGAGGT 180
TGCCAGTGCC GAGTCTAAGG ACCTGACTCC CGGGAAATAC CGGTTGAAGG TTACCAATCT 240
TCAGGACAAC CCGCAGATCG CTCACCCCAG TCACTTACTT                      280
```

FIG.7

```
ACGCGCTACC AAAAGGCAAA GAGTGACGTC TTCCCCTACA GAAGCGCTGT CGGCGCGGAT  60
TCCAATAGCC TGGTGAAAGC CGGCAAATAC GACATGTCGA TGGCCTATAT GGAATATGAG 120
GTTGCCAGTG CCGAGTCTAA GGACCTGACT CCCGGGAAAT ACCGGTTGAA GGTTACCAAT 180
CTTCAGGACA ACCGCAGATC                                             200
```

FIG.10

```
AAAGGGAACA AAAGCTGGAG CTCCACCGCG GTGGCGGCCG CTCTAGCCCA TGTAAGCTCC  60
TGGGGATTCA CGAGCTGAAT CGTGATTTGC CGGCAGTGTG GCAAGGCACG CGCTACCAAA 120
AGGCAAAGAG TGACGTCTTC CCCTACAGAA GCGCTGTCGG CGCGGATTCC AATAGCCTGG 180
TGAAAGCCGG CAAATACGAC ATGTCGATGG CCTATATGGA ATATGAGGTT GCCAGTGCCG 240
AGTCTAAGGA CCTGACTCCC GGGAAATACC GGTTGAAGGT TACCAATCTT CAGGACAACC 300
CGCAGATCGC TCACCCCAGT CACTTACTTG GGCGGATCCC CCGGGCTGCA GGAATTCGAT 360
ATCAAGC                                                           367
```

FIG.11

POLYMERASE CHAIN REACTION-BASED DIAGNOSTIC TEST FOR THE DETECTION OF *XANTHOMONAS CAMPESTRIS* PATHOVAR PELARGONII

BACKGROUND OF THE INVENTION

1. Field of the Invention

The invention relates to methods and reagents for screening plants, particularly geraniums, for infections with bacterial pathogens. Specifically, the invention is related to nucleic acid amplification and detection methods for specifically detecting a certain pathovar of a bacterial infectious agent in geraniums. The invention provides a nucleic acid hybridization probe that is specific for *Xanthomonas campestris* pathovar pelargonii, and paired sets of oligonucleotide primers for polymerase chain reaction (PCR)-catalyzed amplification of DNA fragments comprising the nucleic acid sequences of the invention and specific for *Xanthomonas campestris* pathovar pelargonii. The invention also provides PCR-based methods for detecting *Xanthomonas campestris* pathovar pelargonii DNA, and in particular for distinguishing pathovar DNA from the DNA of the host plant. Methods for producing detectably-labeled hybridization probes using PCR chain reaction are also provided.

2. Background of the Invention

Cultivation of flowering plants is an important economic resource in many countries in the both developed and developing world. However, disease and infestation with a variety of bacterial pathogens causes significant economic losses in this industry. This is particularly true for vegetatively-propagated plants, in which infection of the stock plant can result in infection of all the progeny derived from such plants, as well as vertical propagation to other stock plants.

Geraniums (Pelargonium) are one such vegetatively-propagated plant afflicted with bacterial pathogens. The most important pathogen of geraniums worldwide is *Xanthomonas campestris* pathovar pelargonii (Brown) Dye (Knauss and Tammen, 1967, *Phytopathology* 57: 1178–1181; Strider, 1985, "Geranium" in *Diseases of Floral Crops,* vol. 2., (Strider, ed.), Praeger Publishers: New York, pp. 142–156). This bacterial pathogen is the etiologic agent of bacterial blight, a disease that often causes significant losses to commercial geranium propagators.

Following infection of the plant, the bacteria become distributed systemically in the xylem of the stems, petioles and leaves. Affected plants are characterized by the development of wilting and water-soaked leaf spots, but when cultivated under conditions unfavorable for symptom development, infected plants often remain asymptomatic. Symptomless geraniums may be inadvertently distributed by domestic and international growers through cuttings taken from infected stock plants. American and European growers currently employ a costly and time consuming quarantine and certification procedure to identify geranium stock plants infected with *X. campestris* pathovar pelargonii. However, even with extensive indexing and elaborate quarantine programs, sporadic outbreaks of bacterial blight continue to occur in geraniums.

A variety of methods have been used to detect *X. campestris* pathovar pelargonii in geranium plants, including pathogenicity, biological recovery, and antibody-based tests.

Lazo et al., 1987, *Int. J. Syst. Bacteriol.* 37: 214–221 disclosed the use of restriction fragment length polymorphism to distinguish pathovars of *X. campestris*.

Tuinier, 1989, *Plant Diseases* 73: 875–878 disclosed the use of serological reagents to detect *X. campestris* pathovar pelargonii in aqueous extracts of geranium plants.

Benedict et al., 1990, *Appl. Environ. Microbiol.* 56: 572–574 disclosed pathovar-specific antigens of *X. campestris* pathovar pelargonii detected with monoclonal antibodies.

Anderson & Nameth, 1990, *Phytopathology* 80: 357–360 disclosed the development of a polyclonal antibody-based serodiagnostic assay for the detection of *X. campestris* pathovar pelargonii in geranium plants.

Vauterin et al., 1990, *Syst, Appl. Microbiol.* 13: 166–176 disclose taxonomic analysis of *X. campestris* pathovars by protein electrophoretic and DNA hybridization techniques.

Vauterin et al., 1991, *Gen. Microbiol.* 137: 1766–1787 disclosed grouping of *X. campestris* pathovars by SDS-PAGE analysis of proteins.

Rasmussen & Reeves, 1992, *J. Biotechnol.* 25: 203–220 disclose DNA probes for the detection of plant pathogenic bacteria.

Hartung, 1992, *Plant Diseases* 76: 889–893 disclose plasmid-based hybridization probes for detection and identification of *X. campestris* pathovar citri.

Seal et al., 1992, *Appl. Environ. Microbiol.* 58: 3751–3758 disclosed specific DNA probes and oligonucleotide primers for PCR detection of *Pseudomonas solanacearum* DNA.

More recently, the feasibility of exploiting polymerase PCR amplification to detect laboratory isolates of *X. campestris* pathovar pelargonii has been described.

Manulis et al., 1992, *Phytoparasitica* 2: 263 disclosed the use of random amplified polymorphic DNA methods for identifying *X. campestris* pathovar pelargonii.

Louws et al., *Can. J. Bot.* 14: 245 disclose genomic fingerprinting of *X. campestris* pathovar vesicatoria by PCR of repetitive sequences.

Hartung et al., 1993, *Appl. Environ. Microbiol.* 59: 1143–1148 disclose polymerase chain reaction-based detection assay for *X. campestris* pathovar citri.

Judd et al., 1993, *Appl. Environ. Microbiol.* 59: 1702–1708 disclose the use of PCR amplification of repetitive sequences to genetically classify strains of *Bradyrhizobium japonicum.*

Manulis et al., 1994, Appl. Environ. Microbiol. 60: 4094–4099 disclose the use of PCR methods to detect *X. campestris* pathovar pelargonii with DNA primers and probes identified by random amplified polymorphic DNA analysis.

Sulzinski et al., 1995, *J. Phytopathology* 143: 429–433 disclosed fingerprinting of *Xanthomonas campestris* pathovar pelargonii and related pathovars using random-primed PCR.

The prior art does not describe a rapid, economical, specific and sensitive method, or reagents for implementing such method, for detecting *X. campestris* pathovar pelargonii in cultivated geraniums. Thus, there remains a need in the art for such methods and reagents.

SUMMARY OF THE INVENTION

The present invention provides a PCR-based assay for the specific detection of *Xanthomonas campestris* pathovar pelargonii DNA in a biological sample. The invention provides methods for performing said assay, and oligonucleotide primer pairs that specifically amplify *X. campestris* pathovar pelargonii DNA in a biological sample. The invention also provides a nucleic acid probe for detecting *X. campestris* pathovar pelargonii DNA and amplified fragments therefrom in a biological sample, as well as methods for preparing such probes.

In a first aspect, the invention provides a nucleic acid hybridization probe that specifically hybridizes to genomic DNA of *X. campestris* pathovar pelargonii under high stringency conditions. In a preferred embodiment, the probe comprises an isolated nucleic acid having a nucleotide sequence that is identified by Seq. I.D. No. 7 (shown FIG. 7). In additional preferred embodiments, the hybridization probe of the invention is detectably labeled with biotin or a radioactive, antigenic or fluorescent label.

In a second aspect, the invention provides a pair of oligonucleotide polymerase chain reaction primers derived from the nucleic acid shown in FIG. 7. The primers of the invention are provided to produce a specific nucleic acid fragment having a defined size after PCR using *X. campestris* pathovar pelargonii genomic DNA as a template.

In a preferred embodiment, one of the oligonucleotide primers has the sequence:

5'-ACGCGCTACCAAAAGGCAAAGAG-3' (XcpM1; Seq. I.D. No.: 5).

In another preferred embodiment, one of the oligonucleotide primers has the sequence:

5'-GATCTGCGGTTGTCCTGAAGATTGG-3' (XcpM2; Seq. I.D. No.: 6).

In yet another preferred embodiment, the oligonucleotide primers have the sequence:

5'-ACGCGCTACCAAAAGGCAAAGAG-3' (XcpM1; Seq. I.D. No.: 5)

and

5'-GATCTGCGGTTGTCCTGAAGATTGG-3' (XcpM2; Seq. I.D. No.: 6).

In addition, oligonucleotide primers wherein the specific DNA fragment has a size of 200 base pairs (Seq. I.D. No. 8, shown in FIG. 10) are preferred.

The invention thus provides a method for detecting *Xanthomonas campestris* pathovar pelargonii in a DNA sample. This method comprises the steps of: a) preparing a PCR mixture comprising the DNA sample to be tested, a pair of oligonucleotide primers, and a polymerase; b) performing PCR on said mixture for a number of cycles sufficient to produce a detectable quantity of a specific DNA fragment comprising the nucleic acid identified as Seq. I.D. No.8 (shown in FIG. 10); and c) detecting production of the specific DNA fragment in the reaction mixture. In a preferred embodiment, one of the oligonucleotide primers has the sequence 5'-ACGCGCTACCAAAAGGCAAAGAG-3' (XcpM1; Seq. I.D. No.: 5).

In another preferred embodiment, one of the oligonucleotide primers has the sequence:

5'-GATCTGCGGTTGTCCTGAAGATTGG-3' (XcpM2; Seq. I.D. No.: 6).

In yet another preferred embodiment of the method, the oligonucleotide primers have the sequence:

5' -ACGCGCTACCAAAAGGCAAAGAG-3' (XcpM1; Seq. I.D. No.: 5)

and

5'-GATCTGCGGTTGTCCTGAAGATTGG-3' (XcpM2; Seq. I.D. No.: 6).

In addition, the method is preferably provided wherein the oligonucleotide primers produce a specific DNA fragment having a size of 200 base pairs (Seq. I.D. No. 8). The method also preferably utilizes a thermostable polymerase for catalyzing the PCR.

Detection of the specific DNA fragment in preferred embodiments of the method is achieved by gel electrophoresis and ethidium bromide staining. In additional preferred embodiments, wherein the sensitivity of detection is increased, the specific DNA fragment is detected by blot hybridization with a detectably-labeled specific nucleic acid probe under conditions of high stringency. In the latter preferred embodiments, the hybridization probe preferably comprises a nucleic acid having a nucleotide sequence identified by Seq. I.D. No.7.

In a fourth aspect, the invention provides a method for screening a plant for infection with or contamination by *Xanthomonas campestris* pathovar pelargonii. The method comprising the steps of: a) preparing a bacterial extract from the plant, wherein a portion of the plant comprising stems, petioles, leaves or roots is macerated in an aqueous solution to form a mixture, and a portion of the macerated plant mixture is used to inoculate a bacterial culture solution to yield a bacterial inoculum; b) preparing a DNA sample from the bacterial inoculum; c) preparing a PCR mixture comprising the DNA sample, a pair of oligonucleotide primers, and a polymerase; d) performing PCR on said mixture for a number of cycles sufficient to produce a detectable quantity of a specific DNA fragment comprising a nucleic acid identified by Seq. I.D. No. 8; and e) detecting production of the specific DNA fragment in the reaction mixture. In a preferred embodiment, one of the oligonucleotide primers has the sequence 5'-ACGCGCTACCAAAAGGCAAAGAG-3' (XcpM1; Seq. I.D. No.: 5).

In another preferred embodiment, one of the oligonucleotide primers has the sequence:

5'-GATCTGCGGTTGTCCTGAAGATTGG-3' (XcpM2; Seq. I.D. No.: 6).

In yet another preferred embodiment of the method, the oligonucleotide primers have the sequence:

5'-ACGCGCTACCAAAAGGCAAAGAG-3' (XcpM1; Seq. I.D. No.: 5)

and

5'-GATCTGCGGTTGTCCTGAAGATTGG-3' (XcpM2; Seq. I.D. No.: 6).

In addition, the method is preferably provided wherein the oligonucleotide primers produce a specific DNA fragment having a size of 200 base pairs (Seq. I.D. No. 8). The method also preferably utilizes a thermostable polymerase for catalyzing the PCR.

Detection of the specific DNA fragment in preferred embodiments of the method is achieved by gel electrophoresis and ethidium bromide staining. In additional preferred embodiments, wherein the sensitivity of detection is increased, the specific DNA fragment is detected by blot hybridization with a detectably-labeled specific nucleic acid probe under conditions of high stringency. In the latter preferred embodiments, the hybridization probe preferably comprises a nucleic acid having a nucleotide sequence identified by Seq. I.D. No.7 (FIG. 7).

In a particularly preferred embodiment, the plant to be tested for infection by *X. campestris* pathovar pelargonii is a geranium.

In a preferred embodiment of the method of this aspect of the invention, the bacterial DNA sample is prepared directly from the macerated plant mixture using any of a variety of DNA extraction media. In a preferred embodiment, the extraction media is GeneReleaser™.

In a fifth aspect, the invention provides a recombinant genetic construct comprising a replicable vector covalently linked to a nucleic acid having a nucleotide sequence identified as Seq. I.D. No. 7. The invention also provides a transformed cell comprising the recombinant expression construct of the invention.

In a sixth aspect, the invention provides a method for preparing a nucleic acid hybridization probe that specifically hybridizes to genomic DNA of *X. campestris* pathovar pelargonii under high stringency conditions. The method of this aspect of the invention comprises the steps of: a) preparing a PCR mixture comprising the recombinant genetic construct of the invention, a pair of detectably-labeled polymerase chain reaction primers comprising oligonucleotides having a nucleotide sequence homologous to the nucleotide sequence of the vector flanking the nucleic acid having a nucleotide sequence identified as Seq I.D. No.7, and a polymerase; and b) performing PCR said mixture for a number of cycles sufficient to produce a quantity of a detectably-labeled specific DNA fragment sufficient to comprise a nucleic acid hybridization probe. In a preferred embodiment, one of the oligonucleotides comprising the PCR primers has the sequence:

5'-AAAGGGAACAAAAGCTGGAGC-3' (MAS-3; Seq. I.D. No.: 3).

In another preferred embodiment, one of the oligonucleotides comprising the PCR primers has the sequence:

5'-GCTTGATATCGAATTCCTGCA-3' (MAS-4; Seq. I.D. No.: 4).

In a particularly preferred embodiment, the oligonucleotides comprising the PCR primers have the sequence:

5'-AAAGGGAACAAAAGCTGGAGC-3' (MAS-3; Seq. I.D. No.: 3)

and

5'-GCTTGATATCGAATTCCTGCA-3' (MAS-4; Seq. I.D. No.: 4).

In addition, the method is preferably provided wherein the oligonucleotide primers produce a specific DNA fragment having a size of 367 base pairs (Seq. I.D. No.9, shown in FIG. 11). The method also preferably utilizes a thermostable polymerase for catalyzing the polymerase chain reaction.

Thus, in a seventh aspect, the invention provides a pair of oligonucleotide PCR primers complementary to the nucleotide sequence of the vector comprising the recombinant genetic construct of the invention flanking the nucleic acid insert identified by Seq I.D. No.7, wherein the primers produce a specific nucleic acid fragment having a defined size after PCR using the recombinant genetic construct of the invention as a template. In a preferred embodiment, one of the oligonucleotides comprising the PCR primers has the sequence:

5'-AAAGGGAACAAAAGCTGGAGC-3' (MAS-3; Seq. I.D. No.: 3).

In another preferred embodiment, one of the oligonucleotides comprising the PCR primers has the sequence:

5'-GCTTGATATCGAATTCCTGCA-3' (MAS-4; Seq. I.D. No.: 4).

In a particularly preferred embodiment, the oligonucleotides comprising the PCR primers have the sequence:

5'-AAAGGGAACAAAAGCTGGAGC-3' (MAS-3; Seq. I.D. No.: 3)

and

5'-GCTTGATATCGAATTCCTGCA-3' (MAS-4; Seq. I.D. No.: 4).

In addition, the oligonucleotide PCR primers preferably produce a specific DNA fragment having a size of 367 base pairs (Seq. I.D. No. 9, shown in FIG. 11). In additional preferred embodiments, one of the oligonucleotides is detectably labeled, most preferably with biotin or a radioactive, antigenic or fluorescent label. In other embodiments, the detectable label is incorporated into the nucleic acid hybridization probe during polymerase incorporation of labeled deoxynucleotide triphosphate residues.

The invention provides methods and reagents for detecting the presence of *X. campestris* pathovar pelargonii in biological samples, particularly plants and most particularly geraniums. The invention provides a rapid, sensitive, economical and specific method for screening geranium plants for infection by *X. campestris* pathovar pelargonii. Thus, the invention advantageously provides an improvement on prior art methods for detecting infection with this bacterium, thereby reducing economic and associated losses caused by infection of geranium with *X. campestris* pathovar pelargonii.

Specific preferred embodiments of the present invention will become evident from the following more detailed description of certain preferred embodiments and the claims.

BRIEF DESCRIPTION OF THE DRAWINGS

FIG. 7 depicts the nucleotide sequence of the a 200 basepair fragment (Seq. I.D. No. 7) of *X. campestris* pathovar pelargonii amplified with the PCR primer pair XcpM1and XcpM2 (Seq. I.D. Nos. 1 & 2).

FIG. 10 depicts the nucleotide sequence of a 200 b.p. fragment (Seq. I.D. No. 8) of *X. campestris* pathovar pelargonii DNA amplified with the PCR primer pair XcpM1and XcpM2 (Seq. I.D. Nos. 5 & 6).

FIG. 11 depicts the nucleotide sequence of a 367 b.p. fragment (Seq. I.D. No. 9) of *X. campestris* pathovar pelargonii DNA comprising the phagemid recombinant genetic vector of the invention amplified with the PCR primer pair MAS-3 and MAS-4 (Seq. I.D. Nos. 3 & 4), wherein the primer sequences are complementary to sequences flanking the *X. campestris* pathovar pelargonii insert.

DETAILED DESCRIPTION OF THE PREFERRED EMBODIMENTS

Figure 1:
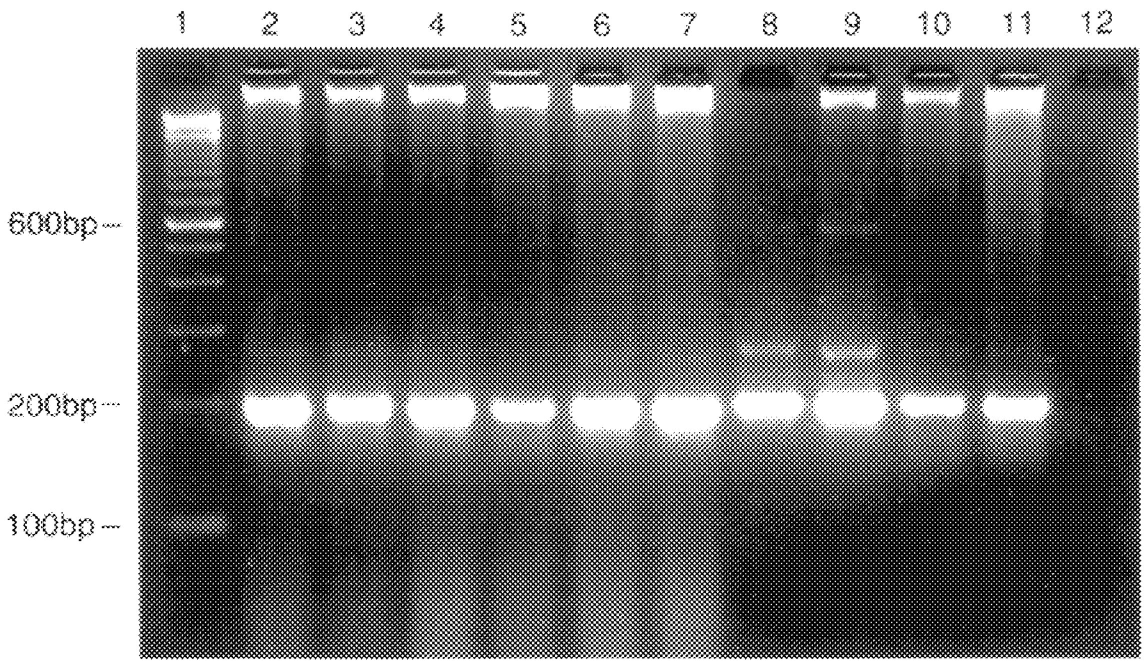
FIG. 1 is a photograph of an ethidium bromide-stained agarose gel illuminated with an ultraviolet transilluminator and showing the PCR amplification products using PCR primers XcpM1and XcpM2 (Seq. I.D. Nos. 5 & 6) from isolates of *X. campestris* pathovar pelargonii. Lane 1: 100 bp DNA ladder; Lane 2: isolate 3; Lane 3: isolate 4; Lane 4: isolate 5; Lane 5: isolate 6; Lane 6: isolate 9; Lane 7: isolate 10; Lane 8: isolate 11; Lane 9, isolate 14; Lane 10, isolate 17; Lane 11, isolate 18; Lane 12, negative control (no template added for amplification).

The present invention provides methods and reagents for detecting a bacterial plant pathogen in extracts from cultivated plants.

In one embodiment of the reagents of the invention are provided nucleic acid hybridization probes. The nucleic acid hybridization probes provided by the invention comprise DNA or RNA embodiments having all or a specifically-hybridizing fragment of the nucleotide sequence of the nucleic acid depicted in FIG. 7 (Seq ID No.:7), or any portion thereof effective in nucleic acid hybridization. Mixtures of such nucleic acid hybridization probes are also within the scope of this embodiment of the invention. Nucleic acid probes as provided herein are useful for detecting the presence of a bacterial infection in a cultivated plant, in contaminated plant samples and specimens, in soil, fertilizer, plant foods, nutrients or additives, in water supplies, or in any substance that may come in to contact with a cultivated plant susceptible to infection by the bacteria. The term "specific hybridization" will be understood to mean that the nucleic acid probes of the invention are capable of stable, double-stranded hybridization to bacterially-derived DNA or RNA under conditions of high stringency, as the term "high stringency" would be understood by those with skill in the art (see, for example, Sambrook et al., 1989, *Molecular Cloning: A Laboratory Manual,* Cold Spring Harbor Laboratory Press, Cold Spring Harbor, N.Y. and Hames and Higgins, eds., 1985, *Nucleic Acid Hybridization,* IRL Press, Oxford, U.K.). Hybridization will be understood to be accomplished using well-established techniques, including but not limited to Southern blot hybridization, Northern blot hybridization, in situ hybridization and, most preferably, Southern hybridization to PCR-amplified DNA fragments.

The invention also provides a nucleic acid hybridization probe comprising a recombinant genetic construct. Production of a nucleic acid hybridization probe as provided by the invention comprising a cloned DNA fragment using genetic engineering means is well known in this art. The discussion which follows is accordingly intended as an overview of this field, and is not intended to reflect the full state of the art.

DNA comprising a nucleic acid hybridization probe of the invention can be prepared, in view of the instant disclosure, by chemical synthesis, by screening genomic libraries from appropriate bacterial cells, or by combinations of these procedures, as illustrated below. Screening of genomic DNA may be carried out with oligonucleotide probes generated from the nucleic acid sequence information from the nucleic acids disclosed herein. Probes may be labeled with a detectable group such as a fluorescent group, a radioactive atom, an antigenic group, a chemiluminescent group or, most preferably, biotin, in accordance with known procedures and used in conventional hybridization assays, as described in greater detail in the Examples below. In a preferred alternative, the nucleic acid hybridization probe of the invention may be obtained by use of the polymerase chain reaction (PCR) procedure, using appropriate pairs of PCR oligonucleotide primers as provided herein corresponding to nucleic acid sequence information derived from the nucleic acid sequence identified as Seq. ID No.: 7. See U.S. Pat. Nos. 4,683,195 to Mullis et al. and 4,683,202 to Mullis.

Cloned embodiments of the nucleic acid hybridization probe DNA of the invention can be replicated in host cells transformed with a recombinant genetic construct comprising a nucleic acid that is the nucleic acids identified as Seq. ID Nos. 7, 8 and 9. Such recombinant genetic constructs are comprised of a vector that is a replicable DNA construct. Vectors are used as disclosed herein to replicate and amplify DNA comprising the nucleic acids of the invention in vivo. For the purposes of this invention, a recombinant genetic construct is a replicable DNA construct in which a nucleic acid insert encoding the nucleic acid hybridization probe identified by Seq. ID Nos. 7, 8 or 9 or fragment thereof is operably linked to suitable control sequences capable of effecting propagation and in vivo amplification of insert DNA. For the purposes of this invention, the term "operatively linked" is intended to encompass a vector covalently linked to insert DNA by at least one end, and preferably both ends, of the insert nucleic acid. The minimal vector sequences comprising the recombinant genetic vectors of the invention are sequences that confer the ability to replicate in a host, typically comprising an origin of replication, and a gene encoding a selectable marker to facilitate recognition of transformants. See, Sambrook et al., 1989, ibid.

Vectors useful for practicing the present invention include plasmids and virus-derived constructs, including phage and particularly bacteriophage and genetically engineered derivatives of phage, particularly phagemids (as provided commercially by Stratagene, La Jolla, Calif.). Typically, the vector replicates and functions independently of the host genome, or, in some instances, is replicated in coordination with host genomic DNA replication. Suitable vectors will contain replicon and control sequences which are derived from species compatible with the intended host cell. A preferred vector is the pCR-Script™ SK(+) cloning vector, derived from the pBluescript® II (SK+) phagemid (and available commercially from Stratagene, La Jolla, Calif.).

Transformed host cells are cells into which have been transferred a replicable recombinant genetic construct made using recombinant DNA techniques. Such constructs can be introduced into the host cell by transformation, transfection, electroporation, or viral transduction, using appropriately matched vectors and methods well known in the art. Preferred host cells are laboratory strains of *Escherichia coli,* including Epicurian Coli® XL-1 Blue MRF' Kan supercompetent cells (available commercially from Stratagene), HB 101 and DH-1α.

The invention provides oligonucleotides for in vitro amplification using any of a variety of amplification protocols known in the art. Preferably, the invention provides oligonucleotides for performing polymerase chain reaction (PCR). See U.S. Pat. Nos. 4,683,195 to Mullis et al. and 4,683,202 to Mullis.

The invention will thus be understood to provide oligonucleotides, specifically, pairs of oligonucleotides, for use as primers for the in vitro amplification of bacterial DNA samples and fragments thereof. In the practice of this invention, the pairs of oligonucleotides herein provided will be understood to comprise two oligonucleotides, comprising from about 8 to about 30 nucleotide residues apiece, said oligonucleotides specifically hybridizing to sequences flanking a nucleic acid to be amplified, wherein the oligonucleotides hybridize to different and opposite strands of the double-stranded DNA target. The oligonucleotides of the invention are preferably derived from the nucleic acid hybridization probe of the invention identified as Seq. ID No. 7. As used in the practice of this invention, the term "derived from" is intended to encompass the development of such oligonucleotides from the nucleic acid sequence of the hybridization probe, from which a multiplicity of alternative and variant oligonucleotides can be prepared. In particular, the invention provides oligonucleotides having a sequence that is substantially complementary to the corresponding sequence of the nucleic acid hybridization probe. As used herein, the term "substantially corresponding to" is intended to encompass oligonucleotides comprising sequence additions, deletions and mismatches, wherein certain nucleotide residues of the oligonucleotide sequence are not optimally complementary (e.g., A-C or G-T) or are non-complementary (e.g., A-G or T-C) to the corresponding sequence of the nucleic acid hybridization probe, provided that such oligonucleotides retain the capacity to specifically amplify the desired insert (as determined by analysis of the fragment size and complexity of the amplified DNA).

The oligonucleotides and nucleic acid hybridization probes of the invention are provided in part for use in methods for detecting *X. campestris* pathovar pelargonii and DNA derived therefrom. Nucleic acids and oligonucleotides of the present invention are useful as diagnostic tools for detecting the existence of a bacterial infection in or on plants, particularly infection of geranium plants with *X. campestris* pathovar pelargonii. Such diagnostic reagents comprise nucleic acid hybridization probes of the invention and encompass paired oligonucleotide PCR primers, as described above. Methods provided by the invention include blot hybridization, in situ hybridization and in vitro amplification techniques for detecting the presence of pathogenic bacteria in a biological sample. Appropriate biological samples advantageously screened using the methods described herein include leaves, stems, roots, petioles, and other portions of a geranium plant. It is also envisioned that the methods of the invention may be used to screen water, soil, fertilizers, plant foods and nutrient additives, and other potential sources of infection.

The invention preferably provides methods for detecting infection of plants, particularly geranium plants, with pathovars of Xanthomonad species, specifically *X. campestris* pathovar pelargonii. The methods of the invention provide for the specific detection of *X. campestris* pathovar pelargonii using a PCR-based assay. In one embodiment of the methods of the invention, *X. campestris* pathovar pelargonii DNA is detected in a DNA sample, such as a laboratory sample or other purified DNA sample. In other embodiments of the methods of the invention, the bacterial nucleic acid is isolated from a bacterial inoculum prepared from a biological source, preferably a geranium plant sample. In the methods of the invention, plant samples, including leaves, stems, roots, petioles and other parts of the geranium plant, are disrupted to disperse the bacteria from the plant tissues and structures. Disruption of plant tissues and structures can be achieved using conventional techniques, including maceration of the plant tissues and structures into an aqueous suspension. Bacteria so liberated from plant tissue are then used to inoculate bacterial culture media and the bacteria grown in the culture media to provide a multiplication of bacterial cells. Bacterial DNA is then prepared from such bacterial cultures using conventional methods.

Alternatively, the invention provides methods for detecting *X. campestris* pathovar pelargonii DNA without such multiplication of bacterial cells. In these embodiments of the methods of the invention, bacterial DNA is isolated directly from bacteria isolated from disrupted plant tissues and structures. In a preferred embodiment, bacterial DNA is directly isolated from dispersed bacteria using commercially-available DNA purification reagents, including the GeneReleaser™ reagent (BioVentures, Inc., Murfreesboro, Tenn.).

In the detection methods of the invention, production of a specific DNA fragment produced by in vitro amplification of a template DNA sample is detected by agarose gel electrophoresis, ethidium bromide staining and ultraviolet transillumination of ethidium bromide stained gels, performed using conventional techniques (Sambrook et al., ibid.), or detection by sequence detection systems using fluorogenic or other labeled probes that rely on automatic or automated detection instrumentation In instances where a greater degree of specificity is required, hybridization of such agarose gels probed with a detectably-labeled nucleic acid hybridization probe of the invention is performed using standard techniques (Sambrook et al., ibid.). In each of these embodiments of the methods of the invention, a sufficient amount of a specific PCR-amplified DNA fragment is produced to be readily detected. For the purposes of this invention, the term "a sufficient amount of a specific PCR-amplified DNA fragment" is defined as that amount required to be detected, either by visualization of ethidium bromide-stained agarose gels or autoradiographic or other development of a blot hybridized with a detectably-labeled probe.

It will be understood that a sufficient quantity of a specific PCR amplified DNA fragment is prepared in PCR amplification reactions by performing a number of cycles required to produce said sufficient amount of the specific DNA fragment. The number of cycles in each PCR required to produce said sufficient amount of a specific DNA fragment will be understood to depend on the oligonucleotide primers, buffers, salts and other reaction components, the amount of template DNA and the PCR cycling times and temperatures. It will also be understood that the optimization of these parameters are within the skill of the worker of ordinary skill to achieve with no more than routine experimentation.

Detectably-labeled probes as provided by the invention are labeled with biotin, a radioisotope (including $^{3}H$, $^{14}C$, $^{35}S$ and $^{32}P$), a fluorescent label (including fluorescein isothiocyanate), and an antigenic label. The detectable label is incorporated into the probe during synthetic preparation of the probe, whereby the probe is alternatively end-labeled or labeled by the incorporation of labeled nucleotides into the synthesized probe.

The invention also provides a PCR-based method for preparing a nucleic acid hybridization probe of the invention. In these embodiments, template DNA comprises a recombinant genetic construct of the invention. A detectably-labeled nucleic acid hybridization probe is prepared by performing PCR amplification using a pair of oligonucleotide primers specific for sequences flanking the position of the nucleic acid insert. Detectable label is incorporated into the nucleic acid hybridization probe by direct end-labeling of PCR primers or incorporation of detectably-labeled nucleotide triphosphates into the probe nucleic acid.

PCR comprising the methods of the invention is performed in a reaction mixture comprising an amount, typically between <10 ng–200 ng template nucleic acid; 50–100 pmoles each oligonucleotide primer; 1–1.25 mM each deoxynucleotide triphosphate; a buffer solution appropriate for the polymerase used to catalyze the amplification reaction; and 0.5–2 Units of a polymerase, most preferably a thermostable polymerase (e.g., Taq polymerse or Tth polymerase).

The invention thus provides diagnostic assays for the specific detection of *X. campestris* pathovar pelargonii. These diagnostic assays include nucleic acid hybridization assays, using the nucleic acids of the invention or specifically-hybridizing fragments thereof, for sensitive detection of bacterial genomic DNA and/or RNA. Such assays include various blot assays, such as Southern blots, Northern blots, dot blots, slot blots and the like, as well as in vitro amplification assays, such as the polymerase chain reaction assay (PCR), reverse transcription-polymerase chain reaction assay (RT-PCR), ligase chain reaction assay (LCR), and others known to those skilled in the art. Specific restriction endonuclease digestion of diagnostic fragments detected using any of the methods of the invention, analogous to restriction fragment linked polymorphism assays (RFLP) are also within the scope of this invention.

The methods of the invention are more fully illustrated in the following Examples. These Examples illustrate certain aspects of the above-described methods and advantageous results. These Examples are shown by way of illustration and not by way of limitation.

EXAMPLE 1

Use of Polymerase Chain Reaction to Detect *Xanthomonas campestris* pathovar pelargonii DNA a. Bacterial sources, culturing and DNA isolation methods Sources of various pathovars of *X. campestris* are shown in Table I. Bacteria were grown in yeast dextrose broth at 22° C. with gentle shaking (100 rpm). Bacterial stocks were stored at −80° C. in 15% glycerol.

DNA was prepared from bacterial cells as follows. Bacterial cells were collected by centrifugation at 3000 g, washed and digested with 2 mg/mL lysozyme and 0.3 mg/mL RNase A for 20 min. at 37° C. to form protoplasts. The protoplasts were lysed with a solution of 1% sodium lauryl sarcosinate, and protein was digested with 0.6 mg/mL Proteinase K at 37° C. for 1 hour. The digested DNA mixture was extracted twice with buffered phenol and twice with chloroform:isoamyl alcohol (24:1 v:v), and DNA precipitated by the addition of 2.5 volumes ethanol. Precipitated DNA was re-dissolved in a solution of 10 mM Tris.HCl (pH 8)/1 mM EDTA.

DNA concentration of each sample was estimated by fluorometry using a minifluorometer (Hoeffer Scientific Instruments, San Francisco, Calif.) according to the manufacturer's instructions.

b. Oligonucleotide primers and PCR conditions

DNA primer pairs used in the experiment disclosed herein are shown in Table II. All primers were custom synthesized by Operon Technologies, Alameda, Calif. using art-established procedures.

PCR amplification of *X. campestris* using the enterobacterial repetitive intergenic consensus sequence primer pair (as modified by Sulzinski et al., 1995, *J. Phytopathology* 143: 429–433 and disclosed in Table II herein as Seq. I.D. Nos. 1 & 2) were as follows. Each 50 μL reaction mixture comprised 100 pmol of each primer, 2.5 μL template DNA (<20–100 ng), 1.25 mM each deoxynucleotide triphosphate, and 1–2U AmpliTaq polymerase (Perkin-Elmer/Cetus) in a buffer provided by the supplier of AmpliTaq and supplemented with 10% dimethyl sulfoxide. PCR amplification was performed in an Eppendorf MicroCycler (Model 100-6700-100; Eppendorf, Fremont, Calif.). PCR reaction conditions were as follows: an initial denaturation step at 95° C. for 7 min, followed by 30 cycles of denaturation (90° C., 30 sec), annealing (52° C., 1 min), and extension (68° C., 8 min), with a final extension step (65° C., 16 min). This reaction scheme is disclosed in Versalovic et al. (1991, *Nucleic Acids. Res.* 19: 6823–6831).

PCR amplification of *X. campestris* DNA using the primer pair XcpM1and XcpM2 (Seq. I.D. Nos. 5 & 6) were performed as follows. Reactions were performed in a 50 μL volume containing 2.5 μL *X. campestris* template DNA (corresponding to <10–200 ng DNA); 100 pmole of each primer; 200 μM of each deoxynucleotide triphosphate (Promega, Madison, Wis.); 2.0 mM $MgCl_2$; and 1.0 Unit of Tfl DNA polymerase (Epicentre Technologies, Madison, Wis.) in Tfl reaction buffer (comprising 50 mM Tris-HCl (pH 9.0)/20 mM ammonium sulfate). Each reaction mixture was overlaid with about 40 μL mineral oil. Negative controls, in which template was replaced with the same volume of sterile distilled water, were included with each amplification. Amplifications were carried out for 1 cycle of 4 min at 94° C., and 30 cycles of 1 min at 94° C. and 1 min at 64° C. PCR amplifications were performed in an Eppendorf MicroCycler Model 100-6700-100 (Eppendorf, Freemont, Calif.).

PCR amplifications with the MAS primer pair (Seq. I.D. Nos. 3 & 4) were carried out in a 25 μL volume containing 1.0 μL of template DNA (<4–80 ng DNA); 50 pmole of each primer; 200 μM of each deoxynucleotide triphosphate; 2.0 mM $MgCl_2$; and 1.0 U of Tfl DNA polymerase in Tfl reaction buffer. Each reaction was overlaid with 20 μL of mineral oil. Amplifications using this primer pair were programmed for 1 cycle of 5 min at 94° C., 5 min at 48° C.; 35 cycles of 90 sec at 72° C., 45 sec at 94° C., and 45 sec at 48° C.; and a final extension for 10 min at 72° C.

c. Nucleic acid fragment analysis and blot hybridization

PCR amplification products were examined by agarose gel electrophoresis. 10 μL of each reaction product were examined on 2% (w:v) agarose gels in Tris-acetate-EDTA (TAE) buffer containing 0.5 g/mL ethidium bromide, as described in Sambrook et al. (1989, *Molecular Cloning: A Laboratory Manual,* Cold Spring Harbor Laboratory Press, Cold Spring Harbor, N.Y.). Gels were electrophoresed for 3–3.5 hr at 70V, and DNA fragments visualized with an ultraviolet transilluminator (Ultraviolet Products Inc., San Gabriel, Calif.) and photographed with a 10–15 s exposure at f4.5 on Polaroid Type 55 film.

For nucleic acid hybridization, gels were treated for 30 min in a solution of 1.5M NaCl/0.5N NaOH followed by 30 min treatment in a solution of 1.0M Tris-HCl (pH 8.0)/1.5M NaCl. Gels were blotted bidirectionally overnight to Nytran immobilization membranes (0.45 μm pore size) (Schleicher & Schuell, Keene, N.H.) pre-wetted in 10 X SSC (1 .5M NaCl/0.15M sodium citrate (pH 7.0)). After transfer, DNA was immobilized to membranes by baking for 30 min at 80° C. Baked membranes were pre-hybridized, hybridized with biotinylated probes (prepared as described below), blocked, washed and visualized with the BluGENE nonradioactive nucleic acid detection system (BRL Life Technologies, Inc., Bethesda, Md.), following the manufacturer's specifications. Colorimetric detection of DNA was carried out at room temperature for 1 h.

d. Cloning and DNA probe preparation

Specific DNA fragments derived from *X. campestris* pathovar pelargonii were cloned and used to prepared nucleic acid hybridization probes as follows. Following PCR amplification of nucleic acid of the Denmark strain 1362 of *Xanthomonas campestris* pathovar pelargonii with the ERIC primer pair (Table II), two amplification products having sizes of ~250 and ~380 base pairs (bp) were extracted from 1% (w:v) low melting temperature agarose gels (FMC BioProducts, Rockland, Me.) after electrophoresis. The gel-purified DNAs were inserted individually into a recombinant phagemid and then used to transform XL1-Blue MRF' $kan^r$ competent *Escherichia coli* cells with the pCR-Script SK(+) cloning kit (Stratagene, La Jolla, Calif.) according to manufacturer's specifications.

Phagemid-specific DNA containing each of the two cloned *X. campestris* inserts was prepared from plaque-purified clones using conventional methods (Sambrook et al., ibid.). Biotin-labeled probes were prepared by extension of biotinylated primers during PCR amplification of the DNA insert within each phagemid. Because ERIC primers would co-amplify any *E. coli* genomic DNA contaminating the phagemid preparation, a different set of amplification primers, designated MAS (Table II; Seq. I.D. Nos. 3 & 4), was designed to target sequences flanking the cloning site on the pCR-Script SK(+) phagemid. Amplification using these primers would thereby amplify insert DNA in the phagemid. Since the MAS primers were each labeled with 5'-biotin, extension of these primers during amplification produced an end-labeled amplicon. After amplification, biotinylated amplicons were separated from unincorporated primers using QIAquick-spin columns (Qiagen, Inc., Chatsworth, Calif.). The two biotinylated amplicons were verified for their specificity for *X. campestris* pathovar pelargonii by hybridization to PRC-amplified products (generated using Seq. I.D. Nos. 1 & 2 as primers) bound to nylon membranes.

e. Experimental Results

1. Specificity of the ERIC-generated amplicons

Two amplification products of *X. campestris* pathovar pelargonii, generated using Seq. I.D. Nos. 1 & 2 as primers and having approximate sizes of 250 and 380 bp, were cloned and used to prepare hybridization probes by extending 5'-biotinylated MAS primers (Sewq. I.D. Nos. 3 & 4) during PCR amplification as described above. Each clone was tested separately for its ability to hybridize specifically to PRC-amplified DNA of the *X. campestri* pathovar pelargonii DNA using Seq. I.D. Nos. 1 & 2 as primers. The probe derived from the 250 bp DNA fragment hybridized to these amplification products from all 19 laboratory isolates of *X. campestris* pathovar pelargonii tested, but did not hybridize to PRC amplification products from 26 other isolates, generated using Seq. I.D. Nos. 1 & 2 as primers, representing ten different pathovars of *X. campestris.* This probe also did not hybridize to such amplification products from isolates of *Erwinia carotovora, Corynebacterium fascians, Pseudomonas cichorii,* or *P. syringae* pathovar syringae.

Due to the apparent specificity of this 250 bp amplification product, the nucleic acid sequence for the cloned insert was determined. This sequence is shown in FIG. 7 (Seq. I.D. No. 7) and comprises a 280 basepair DNA fragment. This sequence was used to design the pathovar-specific amplification primers, XcpM1and XcpM2 (Seq. I.D. Nos. 5 & 6), shown in Table II.

2. Specificity of a PCR-based assay for *Xanthomonas campestris* pathovar pelargonii The XcpM1/XcpM2 primer pair (Seq. I.D. Nos. 5 & 6) was tested in order to determine their pathovar specificity as follows. The primers were used for amplification using as template total nucleic acid of twenty-two geographically-diverse isolates of *X. campestris* pathovar pelargonii. Each isolate tested produced the predicted 200 b.p. amplification product. FIG. 1 displays the amplification products from ten representative isolates of *X. campestris* pathovar pelargonii. The major 200 b.p. (Seq. I.D. No. 8) amplification product was invariably seen with all *X. campestris* pathovar pelargonii targets, thereby demonstrating the robustness and specificity of this PCR-based assay.

In addition to the 200 bp product, a few minor DNAs were occasionally generated from isolates of *X. campestris* pathovar pelargonii, including a 270 bp product (FIG. 1, lanes 8 and 9). The generation of this second amplicon and other larger DNAs varied between isolates and experiments and therefore apparently had no diagnostic significance.

Figure 2:
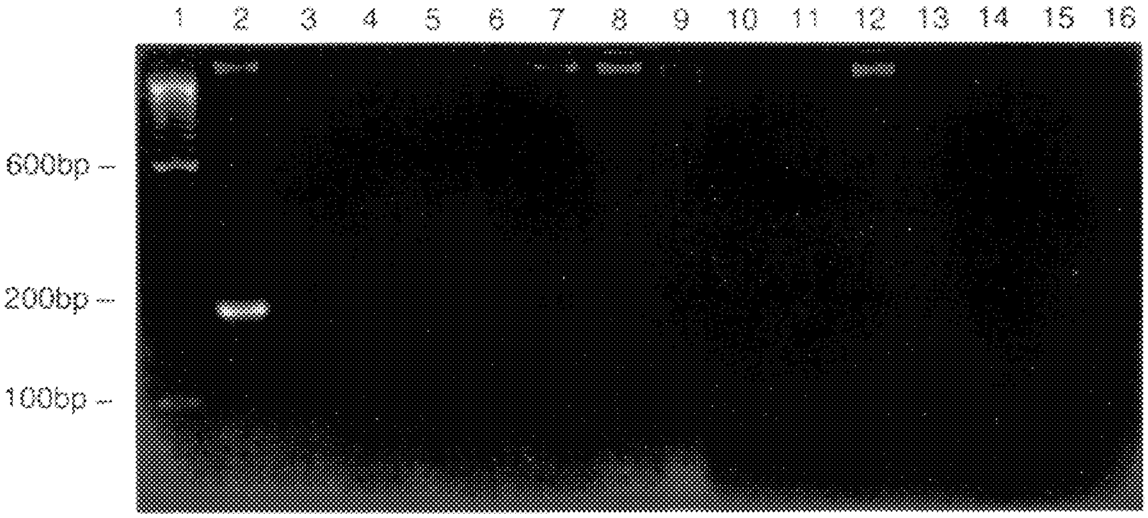
FIG. 2 is a photograph of an ethidium bromide-stained agarose gel illuminated with an ultraviolet transilluminator and showing the PCR amplification products using PCR primers XcpM1and XcpM2 (Seq. I.D. Nos. 5 & 6) obtained with various pathovars of *X. campestris*. Lane 1: 100 bp DNA ladder; Lane 2: *X. campestris* pathovar pelargonii (isolate 3); Lane 3: *X. campestris* pathovar begoniae (isolate 14); Lane 4: *X. campestris* pathovar campestris (isolate P5); Lane 5: *X. campestris* pathovar carotae (isolate 20); Lane 6: *X. campestris* pathovar citri (isolate 2); Lane 7: *X. campestris* pathovar citrumelo (isolate 1); Lane 8: *X. campestris* pathovar juglandis (isolate 17); Lane 9: *X. campestris* pathovar malvacearum (isolate P31); Lane 10: *X. campestris* pathovar manihotis (isolate 15); Lane 11: *X. campestris* pathovar phaseoli (isolate P12); Lane 12: *X. campestris* pathovar pruni (isolate 28); Lane 13: *X. campestris* pathovar vesicatoria (isolate P11); Lane 14: *X. campestris* pathovar vitians B (isolate P18); Lane 15: *X. campestris* pathovar vitians C (isolate P22); Lane 16: negative control (no template added for amplification).

Total nucleic acid fractions of 32 isolates of *X. campestris* representing 12 pathovars (begoniae, campestris, carotae, citri, citrumelo, juglandis, malvacearum, manihotis, phaseoli, pruni, vesicatoria, and vitians) were tested as templates for PCR amplification using the XcpM1/XcpM2 primer pair (Seq. I.D. Nos. 5 & 6). FIG. 2 depicts a representative amplification for each of the 12 pathovars. When isolates of *X. campestris* representing pathovars other than pelargonii were subjected to PCR analysis with this primer pair, most isolates did not generate a visible product upon ethidium bromide staining of agarose gels. A notable exception was the generation of a 200 bp amplification product from two isolates (P19 and P21) of pathovar vitians. However, three other vitians isolates did not generate an amplification product with this primer pair (two such isolates are shown in FIG. 2, lanes 14 and 15). The significance of the occasional amplification of vitians pathovar DNA is unclear.

Figure 3:
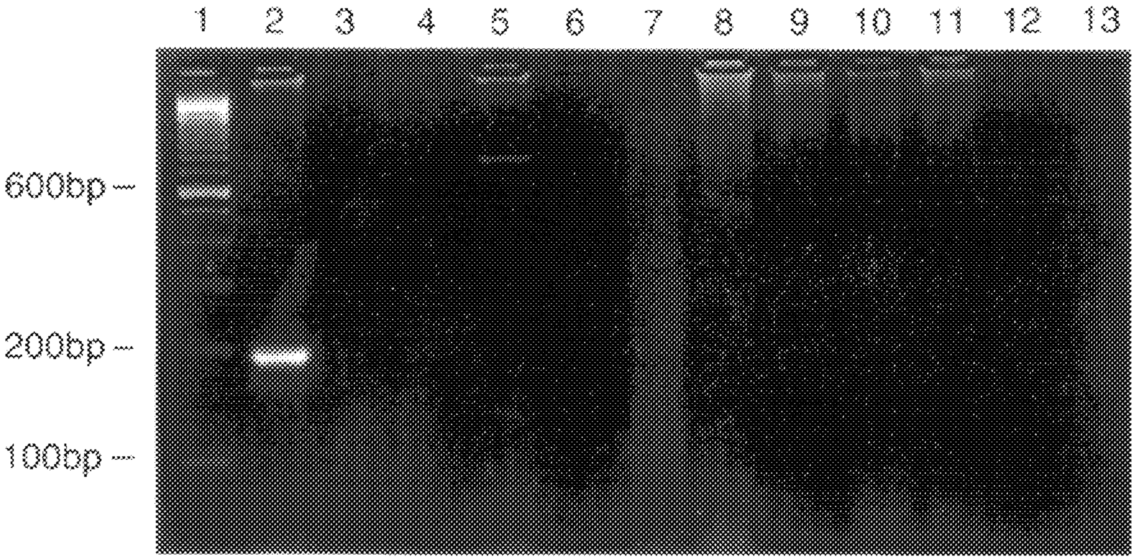
FIG. 3 is a photograph of an ethidium bromide-stained agarose gel illuminated with an ultraviolet transilluminator and showing the PCR amplification products using PCR primers XcpM1and XcpM2 (Seq. I.D. Nos. 5 & 6) obtained with various bacteria outside the genus Xanthomonas. Lane 1:100 bp DNA ladder; Lane 2: *X. campestris* pathovar pelargonii (isolate 3); Lane 3: *Agrobacterium tumefaciens* (isolate G14); Lane 4: *Corynebacterium fascians* (isolate G2); Lane 5: *Erwinia amylovora* (isolate G12); Lane 6: *E. carotovora* subspecies carotovora (isolate G1); Lane 7: *E. chrysanthemi* (isolate G10); Lane 8: *E. herbicola* (isolate G9); Lane 9: *E. stewartii* (isolate G16); Lane 10: *Pseudomonas cichorii* (isolate G5); Lane II: *P. syringae* pathovar glycinea (isolate G19); Lane 12: *P. syringae* pathovar syringae (isolate G18); Lane 13: :negative control (no template added for amplification).

Total nucleic acid from 19 isolates of non-Xanthomonad plant pathogenic bacteria were also tested as templates for PCR amplification; these results are shown in FIG. 3. These isolates represented *Agrobacterium tumefaciens, C. fascians, E. amylovora, E. carotovora* subsp. carotovora, *E. chrysanthemi, E. herbicola, E. stewartii, P. cichorii, P. syringae* pathovar. glycinea, and *P. syringae* pathovar syringae. None of these bacteria generated the diagnostic 200 b.p. product (although one isolate of *E. amylovora* generated a faint higher molecular weight product).

These results demonstrated that the XcpM1/XcpM2 primer pair (Seq. I.D. Nos. 5 & 6) specifically amplified the 200 bp fragment (Seq. I.D. No. 8) from *X. campestris* pathovar pelargonii DNA and did not amplify this fragment from DNA isolated from other Xanthomonas pathovars or other bacterial species. An exception was the generation of a 200 b.p. amplification product from two of five isolates of pathovar vitians. However, since the pathovar vitians is native to lettuce, it is unlikely to be encountered in geraniums in propagation (see below),and thus any potential amplification of this template should have little impact on the utility of this procedure to diagnose *X. campestris* pathovar pelargonii infections in geranium plants. Thus, these results established the XcpM1/XcpM2 primer pair (Seq, I.D. Nos. 5 & 6) as specific amplimers of *X. campestris* pathovar pelargonii DNA.

3. Determination of assay sensitivity

Figure 4:
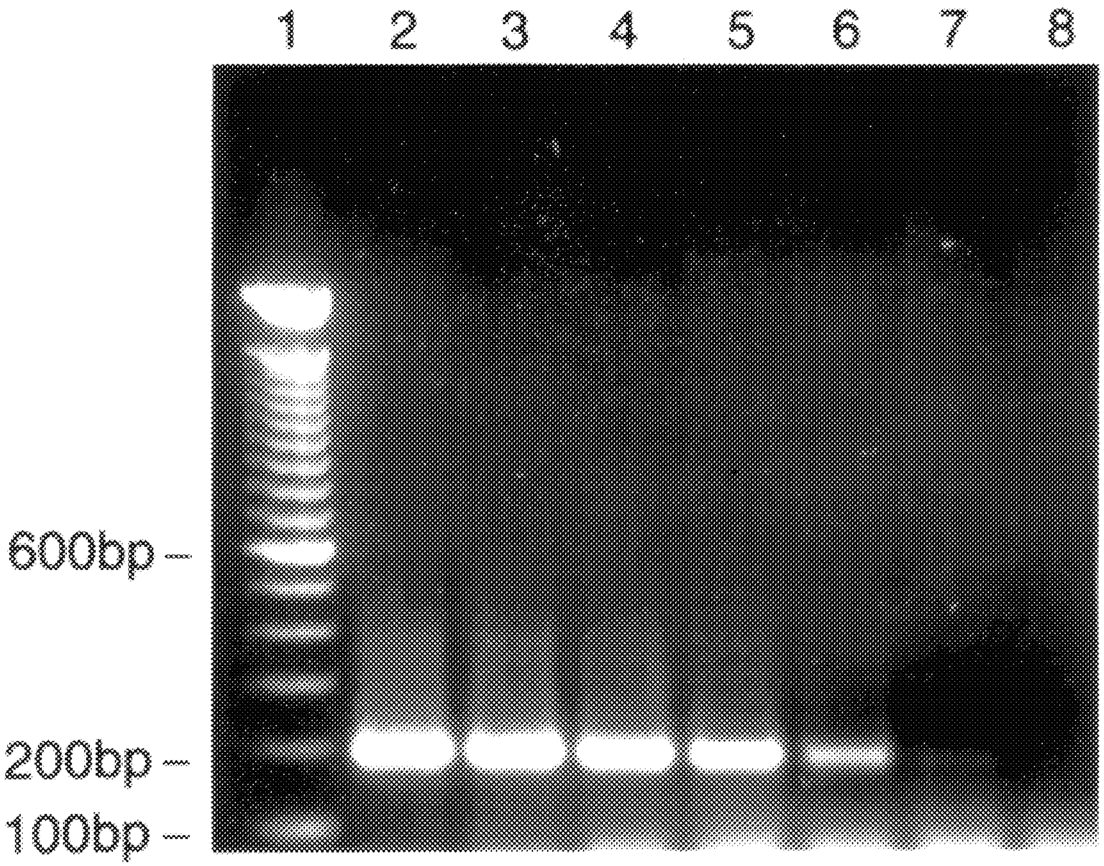
FIG. 4 is a photograph of an ethidium bromide-stained agarose gel illuminated with an ultraviolet transilluminator and showing the PCR amplification products of a titration of *X. campestris* pathovar pelargonii DNA target in a recombinant phagemid amplified with primer set XcpM1and XcpM2 (Seq. I.D. Nos. 5 & 6). PCR amplification was carried out with the indicated copy number of *X. campestris* pathovar pelargonii target DNA as template. Lane 1: 100 bp DNA marker; Lane 2: $1.38\times10^8$ copies; Lane 3: $1.38\times10^7$ copies; Lane 4: $1.38\times10^6$ copies; Lane 5: $1.38\times10^5$ copies; Lane 6: $1.38\times10^4$ copies; Lane 7: $1.38\times10^3$ copies; Lane 8: $1.38\times10^2$ copies.
Figure 5:
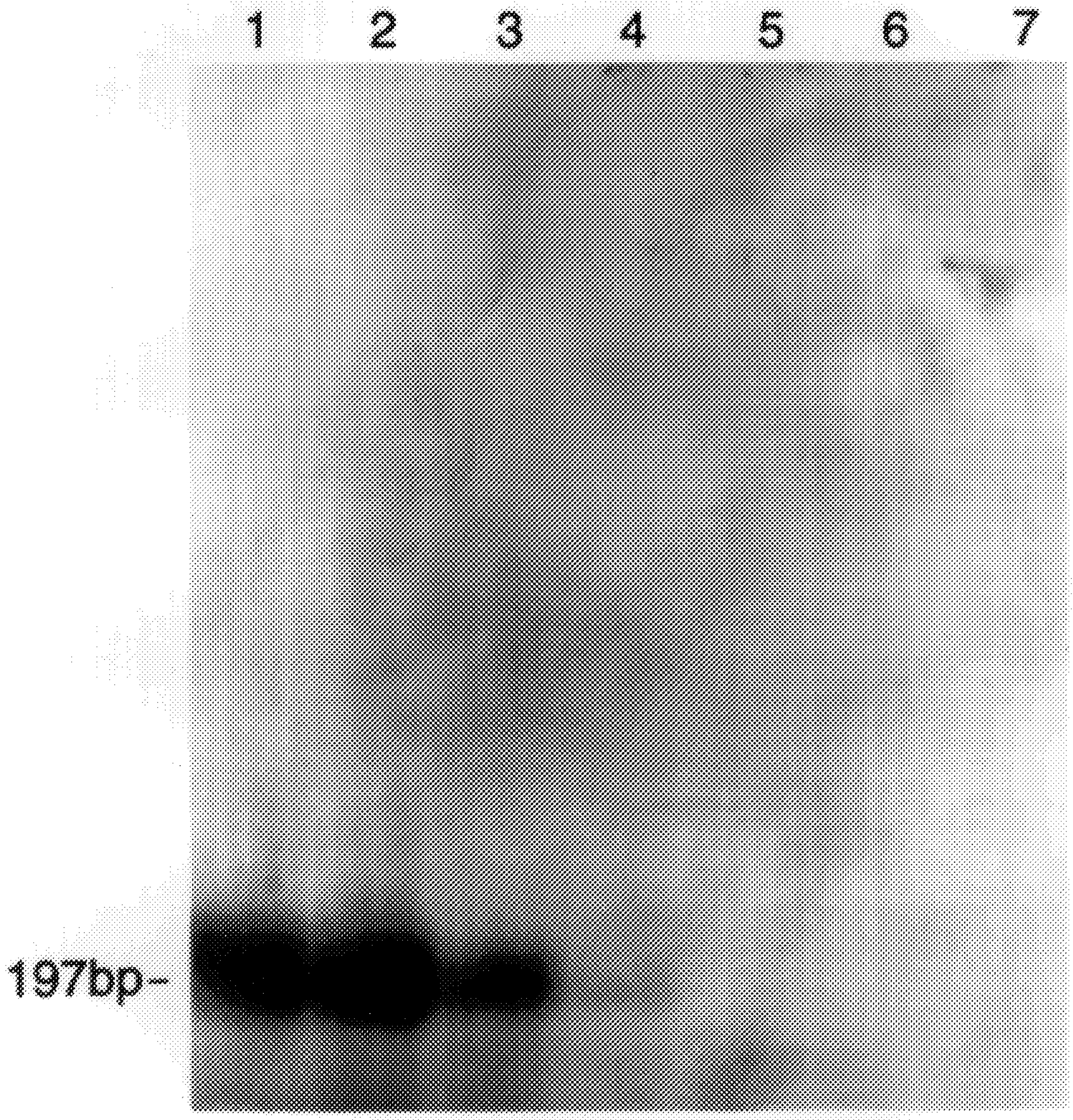
FIG. 5 is a photograph of a Southern blot hybridization using a biotinylated *X. campestris* pathovar pelargonii specific probe (shown in FIG. 11; Seq. I.D. No. 9) prepared using biotinylated primers MAS-3 and MAS-4 (Seq. I.D. Nos. 3 & 4). PCR amplification was performed using *X. campestris* pathovar pelargonii DNA as template, the fragments resolved by agarose gel electrophoresis and Southern blot hybridization performed. The blot shows the results of a titration of *X. campestris* pathovar pelargonii DNA target in a recombinant phagemid amplified with primer set XcpM1and XcpM2 (Seq. I.D. Nos. 5 & 6). PCR amplification was carried out with the indicated copy number of *X. campestris* pathovar pelargonii target DNA as template. Lane 1: 138,000 copies; Lane 2: 13,800 copies; Lane 3: 1,380 copies; Lane 4: 138 copies; Lane 5: 14. The size and position of the PCR product is indicated (200 bp).

To determine the sensitivity of the PCR-based assay using the *X. campestris* pathovar pelargonii DNA-specific XcpM1/XcpM2 primers (Seq. I.D. Nos. 5 & 6), known numbers of the *X. campestris* pathovar pelargonii DNA target were used as template for PCR reactions. Amplification products of these reactions were examined by agarose gel electrophoresis and by Southern blot hybridization with a biotinylated pathovar-specific probe. Between 1,380,000 and copies of a recombinant phagemid containing the 280 bp DNA diluted in STE (10 mM Tris-HCl (pH 8.0)/100 mM NaCl/1 mM EDTA) were amplified using the XcpM1/XcpM2 primer pair (Seq. I.D. Nos. 5 & 6). The 200 b.p. amplicon was visible on ethidium bromide stained gels at a lower limit of between 1,380 and 13,800 input target copies (FIG. 4). After Southern blot hybridization using the biotinylated probe, between 13.8 and 138 input target copies could be detected (FIG. 5).

A similar experiment was carried out using a known number of colony forming units (CFU) of *X. campestris* pathovar pelargonii as template for PCR. After agarose gel electrophoresis and ethidium bromide staining, assay sensitivity was determined to be between 630 and 6,300 input CFU. Sensitivity of the assay was improved to between 63 and 630 input CFU by Southern blotting and hybridization with the biotinylated probe described above.

These results established that the XcpM1/XcpM2 primer pair (Seq. I.D. Nos. 5 & 6) specifically amplified *X. campestris* pathovar pelargonii with a sensitivity in the assay that suggested the assay would be useful in detecting *X. campestris* pathovar pelargonii in geranium stock plants.

EXAMPLE 2

Use of Polymerase Chain Reaction to Detect *Xanthomonas campestris* pathovar pelargonii Infection in Geranium (Pelargonium)

a. Preparation of *X. campestris* pathovar pelargonii DNA from infected geraniums Petioles of geranium plants (Pelargonium *X. hortorum*) were stab-inoculated with a bacterial suspension of *X. campestris* pathovar pelargonii (isolate 3) or mock-inoculated with sterile distilled water. Plants were incubated under greenhouse conditions until symptoms developed (generally 2 to 3 weeks), at which time they were cut at the soil line and macerated individually with an Agdia Roller Ball device (Agdia Inc, Elkhart, Ind.) in a 15×17.5 cm sealed plastic bag (DowBrands L. P., Indianapolis, Ind.) containing 50 mL sterile distilled water. The extract was expressed through Miracloth (Calbiochem, La Jolla, Calif.), centrifuged at 3000×g for 10 min at 24° C., and the resultant pellet resuspended in 2.5 mL water.

One mL of the resuspended pellet was inoculated into 100 mL YDC broth (10 g/L yeast extract/20g/L dextrose/10 g/L calcium carbonate) and incubated with shaking at 100 rpm, 22° C. for 24 h to allow for multiplication of the bacteria (i.e., biological amplification). After this incubation, cells were pelleted and resuspended in 1.5 mL of sterile distilled water. From this cell suspension, a 500 μL aliquot was removed for the isolation of total nucleic acid as described above in Example 1.

b. Detection of *X. campestris* pathovar pelargonii bacteria in planta

Figure 6:
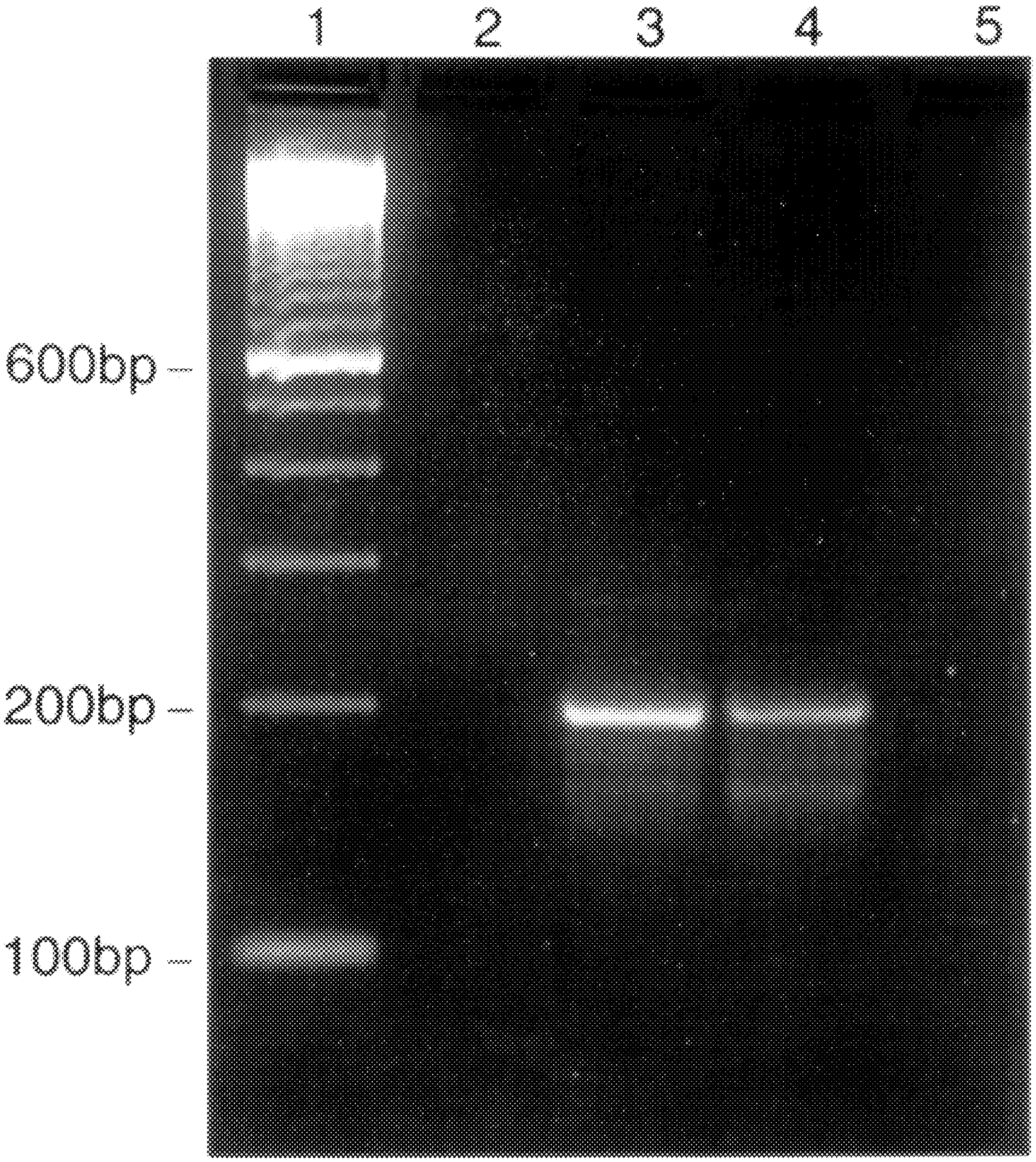
FIG. 6 is a photograph of an ethidium bromide-stained agarose gel illuminated with an ultraviolet transilluminator and showing detection of *X. campestris* pathovar pelargonii in PCR amplified extracts from geranium plants using PCR primers XcpM1and XcpM2 (Seq. I.D. Nos. 5 & 6). Lane 1: 100 bp DNA ladder; Lane 2: PCR amplification products obtained with a total nucleic acid extract from a healthy geranium plant, petiole-stab mock inoculated with water; Lane 3: amplification products from a total nucleic acid extract from a diseased geranium plant, petiole-stab inoculated with *X. campestris* pathovar pelargonii; Lane 4: amplification products from a total nucleic acid extract from *X. campestris* pathovar pelargonii (isolate 3); Lane 5: negative control (no template added for amplification).

PCR amplification of total nucleic acid prepared from a biologically-amplified bacterial fraction from plants infected with *X. campestris* pathovar pelargonii was performed as described in Example 1 using the XcpM1/XcpM2 primer pair (Seq. I.D. Nos. 5 & 6). Such amplification reactions produced the diagnostic 197 bp amplicon (shown in FIG. 6, lane 3). In contrast, comparable nucleic acid preparations from healthy plants that had been mock-inoculated with water did not generate a visible PCR product (FIG. 6, lane 2). Likewise, no DNA products resulted from PCR amplification of nucleic acid preparations from plants infected with other bacterial pathogens of geraniums, such as *C. fascians* and *P. cichorii.*

These results demonstrate that the PCR-based assay using the XcpM1/XcpM2 primer pair (Seq. I.D. Nos. 5 & 6) disclosed herein can detect *X. campestris* pathovar pelargonii infection in geranium plants. This primer pair amplified the target sequence of *X. campestris* pathovar pelargonii to the exclusion of DNA sequences found in the host plant or its resident bacteria. Discrete amplification products were never obtained with nucleic acid preparations from healthy plants or from plants infected with the other bacterial pathogens. These results thus provide verification that the PCR-based assay disclosed herein constitutes a specific, sensitive and robust alternative to methods used in the prior art for screening geraniums for *X. campestris* pathovar pelargonii infection.

EXAMPLE 3

An Alternative Nucleic Acid Extraction Protocol for Preparing Template DNA from *Xanthomonas campestris* pathovar pelargonii for Use in a PCR-based Detection Assay The PCR-based detection assay described in Examples 1 and 2 above was sensitive, specific and robust for *X. campestris* pathovar pelargonii. However, the nucleic acid extraction procedure used here was both time-consuming and laborious, and even after extensive extraction, plant substances inhibitory to PCR amplification were still present in some nucleic acid preparations. For these reasons, the assay described above was determined to be sub-optimal for routine large scale detection of *X. campestris* pathovar pelargonii ex planta. The following extraction protocol was developed to advantageously minimize the inhibitory effect of geranium extracts on PCR amplification, and to escape the requirement for biological amplification of the bacterium prior to PCR.

a. Inoculation of geraniums

Petioles of geranium plants were stab-inoculated as described above in Example 2 with pure culture bacterial suspensions of *X. campestris* pathovar pelargonii (isolate 3), *Corynebacterium fascians* (isolate G4) or *Pseudomonas cichorii* (isolate G2), or with sterile distilled water (mock-inoculated). Plants were incubated under greenhouse conditions for 2–3 weeks for symptom development.

b. Preparation of plant samples

One gram of leaf, petiole and stem tissue from infected or non-infected plants was macerated with an Agdia Roller Ball device (Agdia, Inc., Elkhart, Ind.) in a 15×17.5 cm Ziploc freezer bag (DowBrands L. P., Indianapolis, Ind.) containing 7.5 mL of either distilled water or 10 mM Tris-HCl (pH 8.0). Five microliters of the macerate were added to 20 μL of GeneRelease™ reagent (BioVentures, Inc., Murfreesboro, Tenn.) in 500 μL thin-walled microcentrifuge tubes, vortexed for 5 sec and then heated for 6 min at high power (900 W) in a Sharp model R-4A95 microwave oven. Heated tubes were centrifuged at full speed for 30 sec in an Eppendorf model 5415C microcentrifuge. The upper 5 μL of the supernatant, either undiluted or diluted 1 part to 9 parts of either distilled water or 10 mM Tris-HCl (pH 8.0) (depending on DNA yield) was used as template for PCR amplification as follows.

c. PCR amplification

Primers XcpM1and XcpM2 (Table II; Seq. I.D. Nos. 5 & 6) were used at a concentration of 100 pmole each in a modified amplification master mixture that also included 0.2X rTth reverse transcriptase buffer (20 mM Tris-HCl (pH 8.3)/180 mM KCl) (Perkin Elmer Corp., Norwalk, Conn.); 0.8X rTth chelating buffer (40% (v/v) glycerol/80 mM Tris-HCl (pH 8.3)/0.8M KCl/6.0 mM EGTA/0.4% (v/v) Tween-20) (Perkin Elmer); 40 μM of each deoxynucleotide triphosphate (Promega, Madison, Wis.) 1.5 mM $MgCl_2$; and 1.0 U of Tth DNA polymerase (Epicentre Technologies, Madison, Wis.). To each reaction tube, 45 μL of this master mixture, 5 μL plant extract treated with GeneReleaser™ and 50 μL of mineral oil were added sequentially. An amplification negative control, in which plant extract was replaced by sterile distilled water, and a positive control, in which plant extract was replaced by total genomic nucleic acid of *X. campestris* pathovar pelargonii, was included in each experiment.

PCR amplifications were performed in a Perkin Elmer model 480 thermal cycler programmed for 1 cycle of 2 min at 94° C., and 30 cycles of 1 min at 94° C. and 1 min at 65° C. Amplification products were examined by agarose gel electrophoresis and ethidium bromide staining as described above.

d. Experimental Results

Figure 8:
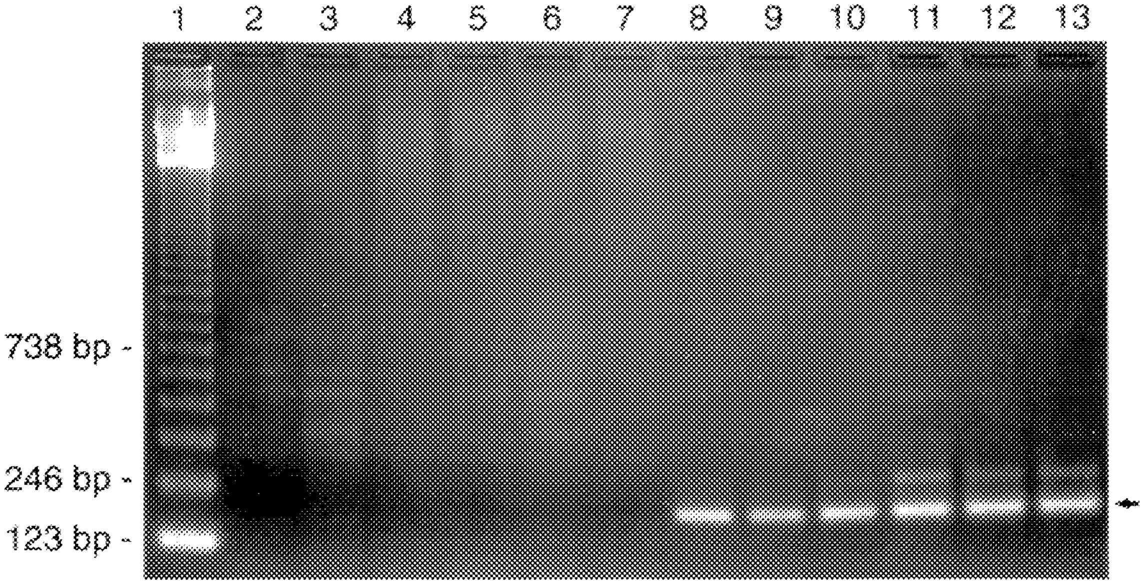
FIG. 8 is a photograph of an ethidium bromide-stained agarose gel illuminated with an ultraviolet transilluminator and showing detection of *X. campestris* pathovar pelargonii in PCR amplified extracts from geranium plants using PCR primers XcpM1and XcpM2 (Seq. I.D. Nos. 5 & 6). Lane 1: 123 bp DNA ladder; Lanes 2–7: amplification products obtained from extracts of six non-infected geraniums; Lanes 8–13: amplification products obtained from extracts of six geraniums infected with *X. campestris* pathovar pelargonii. Arrow indicates the migration position for the diagnostic 200 b.p. *X. campestris* pathovar pelargonii PCR amplicon.

PCR amplification using total nucleic acid samples prepared from plants using GeneReleaser™ allowed the accurate identification of six infected plants (FIG. 8, lanes 8–13) and six non-infected plants (FIG. 8, lanes 2–7). The diagnosis was based on the presence or absence of the 200 base pair (bp) amplification product observed from amplifications with this primer pair and *X. campestris* pathovar pelargonii genomic nucleic acid template.

Figure 9:
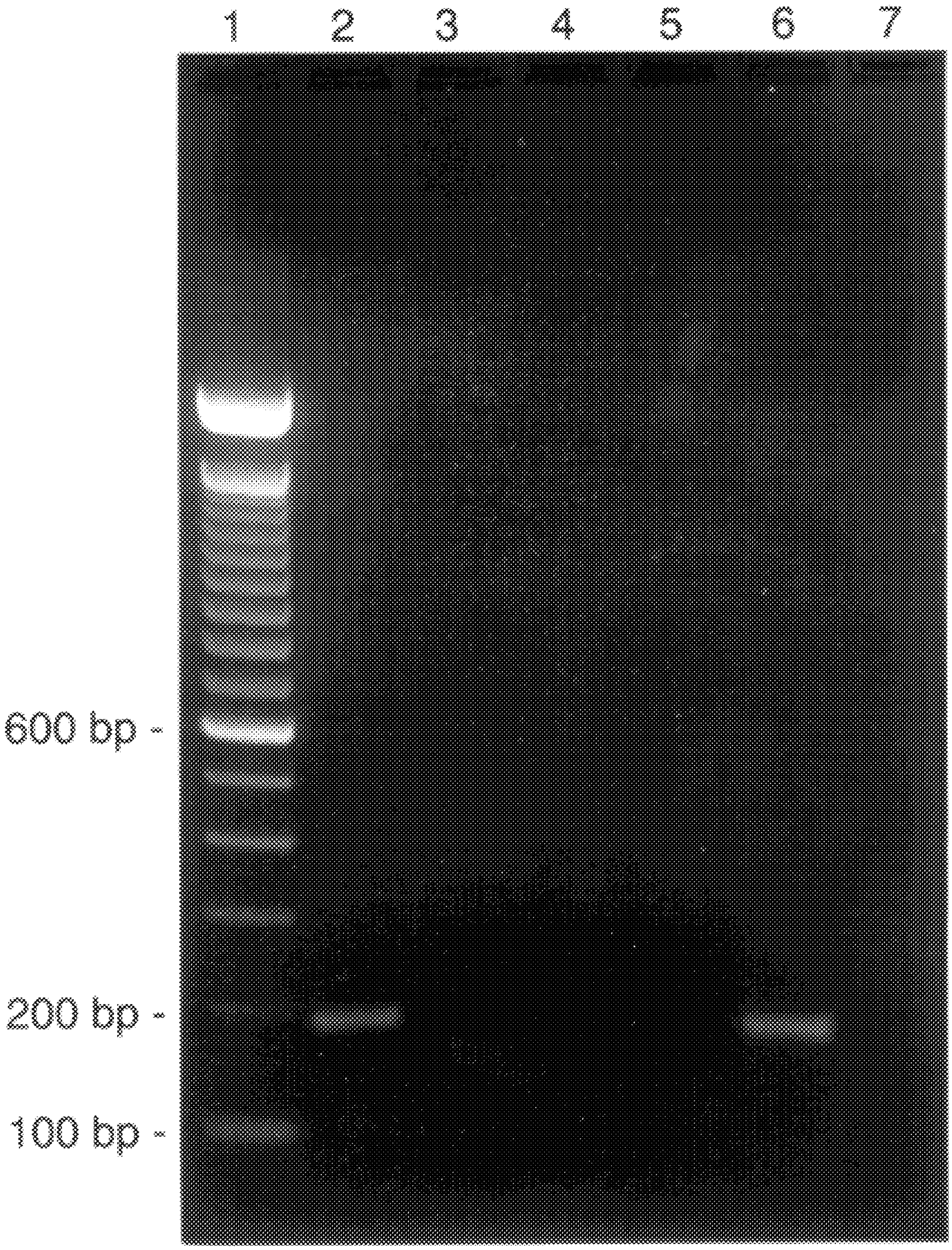
FIG. 9 is a photograph of an ethidium bromide-stained agarose gel illuminated with an ultraviolet transilluminator and showing PCR amplification products obtained from geraniums infected by different bacterial pathogen using PCR primers XcpM1and XcpM2 (Seq. I.D. Nos. 5 & 6). Lane 1, 100 bp DNA ladder; Lane 2, plant infected with *X. campestris* pathovar pelargonii; Lane 3, plant infected with *P. cichorii;* Lane 4, plant infected with *C. fascians*; Lane 5, non-infected plant; Lane 6, PCR positive control, *X. campestris* pathovar pelargonii purified genomic nucleic acid template; Lane 7, negative control (no template added for amplification).

The utility of this extraction-amplification protocol for the specific detection of *X. campestris* pathovar pelargonii explanta was evaluated in experiments with two other common bacterial pathogens of geraniums, *C. fascians* and *P. cichorii.* These results are shown in FIG. 9. The characteristic 200 bp amplicon was observed only from geraniums infected with *X. campestris* pathovar pelargonii (FIG. 9, lane 2) and the amplification-positive control sample (lane 6). No visible amplification products were detected from plants infected with *P. cichorii* (lane 3) or *C. fascians* (lane 4), mock-inoculated with water (lane 5), or from the amplification negative control (lane 7).

These results demonstrate the development of a rapid, economical and technically-easy method for preparing nucleic acid that is useful as an amplification target. Using this method, a confirmatory clinical diagnosis of bacterial blight can be determined in less than 3 hours. The development of this rapid extraction-PCR amplification protocol makes practical large-scale screening and detection efforts for the detection of *X. campestris* pathovar pelargonii in geraniums. The presence or absence of the 200 bp amplification product provides an immediate diagnostic indication for the presence or absence of frank *X. campestris* pathovar pelargonii infection, wherein the amplification product can be observed with ethidium bromide-stained agarose gel electrophoresis. For the detection of more occult or latent infection, the sensitivity of the assay can be increased by Southern blot hybridization with a pathovar-specific biotinylated probe as described above. Widespread use of this assay can be applied to detect asymptomatic infections, eliminating or curtailing the costly quarantine and certification program currently used.

It should be understood that the foregoing disclosure emphasizes certain specific embodiments of the invention and that all modifications or alternatives equivalent thereto are within the spirit and scope of the invention as set forth in the appended claims.

TABLE 1

Bacterial isolates

| Identification Number | Isolate name | Description |
|---|---|---|
| 7 | 77142 | X.c. pv. *pelargonii* |
| 12 | 80483-93 | X.c. pv. *pelargonii* |
| 16 | XCP8 New York strain 1799 | X.c. pv. *pelargonii* |
| P 4 | 69809-88 | X.c. pv. *campestris* |
| P 5 | 22673-89 | X.c. pv. *campestris* |
| P11 | 69802-88 | X.c. pv. *vesicatoria* |
| P12 | 80473-93 | X.c. pv. *phaseoli* |
| P18 | 80479-93 | X.c. pv. *vitians B* |
| P19 | 80480-93 | X.c. pv. *vitians B* |
| P21 | 80484-93 | X.c. pv. *vitians C* |
| P24 | 80487-93 | X.c. pv. *juglandis* |
| P25 | 80488-93 | X.c. pv. *begoniae* |
| P26 | 80489-93 | X.c. pv. *carotae* |
| P29 | XppXpw (CUCPB 0378) | X.c. pv. *phaseoli* |
| P30 | XV-21 (CU0207) | X.c. pv. *vesicatoria* |
| P31 | Xm 14 (CU0241) | X.c. pv. *malvacearum* |
| P32 | CIAT 1134 (CU0206) | X.c. pv. *manihotis* |
| G 1 | 80424-93 | *Erwinia caratovora* pv. *caratovora* |
| G 2 | 32179-88 | *Corynebacterium fascians* |
| G 3 | 32179-88 | *Corynebacterium fascians* |
| G 4 | PC 10 Chrysanth. 082-39 | *Pseudomonas cichorii* |

TABLE 1-continued

Bacterial isolates

| Identification Number | Isolate name | Description |
|---|---|---|
| G 5 | PC 21 Syngonium P27 | *P. cichorii* |
| G 6 | PSS 4 CHII B | *P. syringae* pv. *syringae* |
| G 7 | PSS 35 Tomato 85-15 | *P. syringae* pv. *syringae* |
| G 8 | C649 (A. Collmer G514) | *Agrobacterium tumefaciens* |
| G 9 | 352 CUCPB2050 (apple) | *Erwinia herbicola* |
| G10 | EC16 Collmer F-7 | *E. chrysanthemi* |
| G11 | Ea223 CU0035 (pear) | *E. amylovora* |
| G12 | Ea227 CUCPB0039 (pear) | *E. amylovora* |
| G13 | Ea338 CU0285 (quince) | *E. amylovora* |
| G14 | Atu C58 CU0312 | *A. tumefaciens* |
| G15 | E caro DB17 CU2261 | *E. carotovora* subsp. *carotovora* |
| G16 | DC283 CU3662 | *E. stewartii* |
| G17 | Psy B728a | *P. syringae* pv. *syringae* |
| G18 | Psy Y30 | *P. syringae* pv. *syringae* |
| G19 | PsyRace O CU3393 | *P. syringae* pv. *glycinea*, race O |

TABLE II

Oligonucleotide Primers used for Amplification

ERIC1R(5'-ATGTAAGCTCCTGGGGTTCAC-3')
ERIC2'(5'-AAGTAAGTGACTGGGGTGAGC-3')
MAS-3 (5'-Biotin-AAAGGGAACAAAAGCTGGAGC-3')
MAS-4 (5'-Biotin-GCTTGATATCGAATTCCTGCA-3'
XcpM1 (5'-ACGCGCTACCAAAAGGCAAAGAG-3')
XcpM2 (5'-GATCTGCGGTTGTCCTGAAGATTGG-3')

What we claim is:

1. A nucleic acid hybridization probe that specifically hybridizes to genomic DNA of *Xanthomonas campestris* pathovar pelargonii under high stringency conditions, wherein the probe comprises a nucleic acid having a nucleotide sequence identified by Seq. I.D. No.7.

2. A pair of oligonucleotide PCR primers derived from a nucleic acid having a nucleotide sequence identified by Seq. I.D. No.7, wherein the primers produce a specific nucleic acid fragment having a defined size after PCR using *Xanthomonas campestris* pathovar pelargonii genomic DNA as a template.

3. A pair of oligonucleotide primers according to claim 2, wherein one of the oligonucleotide primers has the sequence:

5'-ACGCGCTACCAAAAGGCAAAGAG-3' (Seq. I.D. No.: 5).

4. A pair of oligonucleotide primers according to claim 2, wherein one of the oligonucleotide primers has the sequence:

5'-GATCTGCGGTTGTCCTGAAGATTGG-3' (Seq. I.D. No.: 6).

5. A pair of oligonucleotide primers according to claim 2, wherein oligonucleotide primers have the sequence:

5'-ACGCGCTACCAAAAGGCAAAGAG-3' (Seq. I.D. No.: 5)

and

5'-GATCTGCGGTTGTCCTGAAGATTGG-3' (Seq. I.D. No.: 6).

6. The oligonucleotide primer pair of claim 5, wherein the specific DNA fragment has a size of 200 base pairs.

7. A method for detecting *Xanthomonas campestris* pathovar pelargonii in a DNA sample, the method comprising the steps of:

a) preparing a PCR mixture comprising the DNA sample, a pair of oligonucleotide primers according to claim 2 and a polymerase;

b) performing PCR on said mixture for a number of cycles sufficient to produce a detectable quantity of a specific DNA fragment comprising the nucleic acid identified as Seq. I.D. No.8; and c) detecting production of the specific DNA fragment in the reaction mixture.

8. The method of claim 7, wherein the oligonucleotide primers are the primers of claim 3.

9. The method of claim 7, wherein the oligonucleotide primers are the primers of claim 4.

10. The method of claim 7, wherein the oligonucleotide primers are the primers of claim 5.

11. The method of claim 10, wherein the specific DNA fragment has a size of 200 base pairs.

12. The method of claim 7, wherein the polymerase is a thermostable polymerase.

13. The method of claim 7, wherein the specific DNA fragment is detected by gel electrophoresis and ethidium bromide staining.

14. The method of claim 7, wherein the specific DNA fragment is detected by blot hybridization with a detectably-labeled specific nucleic acid probe under conditions of high stringency.

15. The method of claim 14 wherein the probe comprises a nucleic acid having a nucleotide sequence identified by Seq. I.D. No. 9.

16. A method for screening a plant for infection with *Xanthomonas campestris* pathovar pelargonii, the method comprising the steps of:

a) preparing a bacterial extract from the plant, wherein a portion of the plant comprising stems, petioles, leaves or roots is macerated in an aqueous solution to form a mixture, and a portion of the macerated plant mixture is used to inoculate a bacterial culture solution to yield a bacterial inoculum;

b) preparing a DNA sample from the bacterial inoculum;

c) preparing a PCR mixture comprising the DNA sample, a pair of oligonucleotides according to claim 2 and a polymerase;

d) performing PCR on said mixture for a number of cycles sufficient to produce a detectable quantity of a specific DNA fragment comprising the nucleic acid identified as Seq. I.D. No.8; and c) detecting production of the specific DNA fragment in the reaction mixture.

17. The method of claim 16, wherein the oligonucleotide primers are the primers of claim 3.

18. The method of claim 16, wherein the oligonucleotide primers are the primers of claim 4.

19. The method of claim 16, wherein the oligonucleotide primers are the primers of claim 5.

20. The method of claim 19, wherein the specific DNA fragment has a size of 200 base pairs.

21. The method of claim 16, wherein the polymerase is a thermostable polymerase.

22. The method of claim 16, wherein the specific DNA fragment is detected by gel electrophoresis and ethidium bromide staining.

23. The method of claim 16, wherein the specific DNA fragment is detected by blot hybridization with a detectably-labeled specific nucleic acid probe under conditions of high stringency.

24. The method of claim 23 wherein the probe comprises a nucleic acid having a nucleotide sequence identified by Seq. I.D. No. 9.

25. A recombinant genetic construct comprising a replicable vector covalently linked to a nucleic acid having a nucleotide sequence identified as Seq. I.D. Nos. 7, 8 or 9.

26. A transformed cell comprising the recombinant genetic construct of claim 25.

27. A method for preparing a nucleic acid hybridization probe that specifically hybridizes to genomic DNA of *Xanthomonas campestris* pathovar pelargonii under high stringency conditions, the method comprising the steps of:

a) preparing a polymerase chain reaction mixture comprising the recombinant genetic construct of claim 25, a pair of detectably-labeled polymerase chain reaction primers comprising oligonucleotides having a nucleotide sequence complementary to the nucleotide sequence of the vector flanking the nucleic acid having a nucleotide sequence identified as Seq I.D. No.7, and a polymerase; and b) performing polymerase chain reaction on said mixture for a number of cycles sufficient to produce a quantity of a detectably-labeled specific DNA fragment sufficient to comprise a nucleic acid hybridization probe.

28. The method of claim 27, wherein one of the oligonucleotides comprising the polymerase chain reaction primers has the sequence:

5'-AAAGGGAACAAAAGCTGGAGC-3' (Seq. I.D. No.: 3).

29. The method of claim 27, wherein one of the oligonucleotides comprising the polymerase chain reaction primers has the sequence:

5'-GCTTGATATCGAATTCCTGCA-3' (Seq. I.D. No.: 4).

30. The method of claim 27, wherein the oligonucleotides comprising the polymerase chain reaction primers have the sequence:

5'-AAAGGGAACAAAAGCTGGAGC-3' (Seq. I.D. No.: 3)

and

5'-GCTTGATATCGAATTCCTGCA-3' (Seq. I.D. No.: 4).

31. The method of claim 27, wherein the specific DNA fragment has a size of 367 base pairs.

32. The method of claim 27, wherein the polymerase is a thermostable polymerase.

33. The method of claim 16, wherein the DNA sample of subpart (b) is prepared from the macerated plant mixture of subpart (a).

34. The method of claim 16 wherein the plant is a geranium.

* * * * *

UNITED STATES PATENT AND TRADEMARK OFFICE

CERTIFICATE OF CORRECTION

PATENT NO. : 5,863,731 Page 1 of 1
APPLICATION NO. : 08/742297
DATED : January 26, 1999
INVENTOR(S) : C. Peter Romaine et al.

It is certified that error appears in the above-identified patent and that said Letters Patent is hereby corrected as shown below:

Column 1, Line 6, after the Title, and before “BACKGROUND OF THE INVENTION” insert the following:

--GOVERNMENT SPONSORSHIP

This invention was made with Government support under Hatch Act Project No. PEN03457 awarded by the United States Department of Agriculture. The Government has certain rights in the invention.--

Signed and Sealed this

Fourteenth Day of April, 2009

JOHN DOLL
*Acting Director of the United States Patent and Trademark Office*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

-continued

ATGTAAGCTC CTGGGGATTC AC 22

( 2 ) INFORMATION FOR SEQ ID NO:2:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

AAGTAAGTGA CTGGGGTGAG C 21

( 2 ) INFORMATION FOR SEQ ID NO:3:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

AAAGGGAACA AAAGCTGGAG C 21

( 2 ) INFORMATION FOR SEQ ID NO:4:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

GCTTGATATC GAATTCCTGC A 21

( 2 ) INFORMATION FOR SEQ ID NO:5:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

ACGCGCTACC AAAAGGCAAA GAG 23

( 2 ) INFORMATION FOR SEQ ID NO:6:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

GATCTGCGGT TGTCCTGAAG ATTGG 25

( 2 ) INFORMATION FOR SEQ ID NO:7:

-continued ( i ) SEQUENCE CHARACTERISTICS:
( A ) LENGTH: 280 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

```
ATGTAAGCTC CTGGGGATTC ACGAGCTGAA TCGTGATTTG CCGGCAGTGT GGCAAGGCAC     60
GCGCTACCAA AAGGCAAAGA GTGACGTCTT CCCCTACAGA AGCGCTGTCG GCGCGGATTC    120
CAATAGCCTG GTGAAAGCCG GCAAATACGA CATGTCGATG GCCTATATGG AATATGAGGT    180
TGCCAGTGCC GAGTCTAAGG ACCTGACTCC CGGGAAATAC CGGTTGAAGG TTACCAATCT    240
TCAGGACAAC CCGCAGATCG CTCACCCCAG TCACTTACTT                          280
```

( 2 ) INFORMATION FOR SEQ ID NO:8:

( i ) SEQUENCE CHARACTERISTICS:
( A ) LENGTH: 200 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

```
ACGCGCTACC AAAAGGCAAA GAGTGACGTC TTCCCCTACA GAAGCGCTGT CGGCGCGGAT     60
TCCAATAGCC TGGTGAAAGC CGGCAAATAC GACATGTCGA TGGCCTATAT GGAATATGAG    120
GTTGCCAGTG CCGAGTCTAA GGACCTGACT CCCGGGAAAT ACCGGTTGAA GGTTACCAAT    180
CTTCAGGACA ACCGCAGATC                                                200
```

( 2 ) INFORMATION FOR SEQ ID NO:9:

( i ) SEQUENCE CHARACTERISTICS:
( A ) LENGTH: 367 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

```
AAAGGGAACA AAAGCTGGAG CTCCACCGCG GTGGCGGCCG CTCTAGCCCA TGTAAGCTCC     60
TGGGGATTCA CGAGCTGAAT CGTGATTTGC CGGCAGTGTG GCAAGGCACG CGCTACCAAA    120
AGGCAAAGAG TGACGTCTTC CCCTACAGAA GCGCTGTCGG CGCGGATTCC AATAGCCTGG    180
TGAAAGCCGG CAAATACGAC ATGTCGATGG CCTATATGGA ATATGAGGTT GCCAGTGCCG    240
AGTCTAAGGA CCTGACTCCC GGGAAATACC GGTTGAAGGT TACCAATCTT CAGGACAACC    300
CGCAGATCGC TCACCCCAGT CACTTACTTG GGCGGATCCC CCGGGCTGCA GGAATTCGAT    360
ATCAAGC                                                              367
```